United States Patent [19]
Furia et al.

[11] Patent Number: 5,792,059
[45] Date of Patent: Aug. 11, 1998

[54] INTRAOPERATIVE PROBE, SPECIFICALLY INTENDED FOR DIRECT-CONTACT OBSERVATIONS

[75] Inventors: Roberto Furia; Francesco Pomata, both of Genoa, Italy

[73] Assignee: Esaote S.p.A., Casale Monferrato, Italy

[21] Appl. No.: 756,796

[22] Filed: Nov. 26, 1996

[51] Int. Cl.$^6$ ........................................ A61B 8/00
[52] U.S. Cl. .................................................. 600/459
[58] Field of Search .............................. 600/459, 461, 600/462, 463, 464

[56] References Cited

U.S. PATENT DOCUMENTS

| | | | |
|---|---|---|---|
| 4,742,829 | 5/1988 | Law | 128/660 |
| 4,877,033 | 10/1989 | Seitz, Jr. | 128/660.05 |
| 4,898,177 | 2/1990 | Takano et al. | 128/662.03 |
| 4,972,839 | 11/1990 | Angelsen | 600/462 |
| 5,070,881 | 12/1991 | Weiland | 128/662.03 |
| 5,088,500 | 2/1992 | Wedel et al. | 128/662.06 |
| 5,176,140 | 1/1993 | Kami | 128/662.03 |
| 5,211,176 | 5/1993 | Ishiguro | 128/662.06 |
| 5,257,628 | 11/1993 | Ishiguro | 128/662.06 |
| 5,381,795 | 1/1995 | Nordgren | 128/663.01 |
| 5,402,793 | 4/1995 | Gruner | 128/660.1 |
| 5,482,047 | 1/1996 | Nordgren | 128/662.03 |
| 5,544,660 | 8/1996 | Crowley | 128/662.06 |
| 5,671,747 | 9/1997 | Connor | 128/662.06 |

*Primary Examiner*—George Manuel
*Attorney, Agent, or Firm*—Baker & Daniels

[57] ABSTRACT

An intraoperative probe, specifically intended for direct-contact observations, includes a head for housing the transducers (T) and a portion of a handle or grip, as well as a cable for connecting the transducers (T) to processing and/or displaying devices. According to the invention, said portion of the handle or grip is separate from the transducer-carrying head, as said two parts are equipped with matching means of removable attachment. The invention also provides for a set of accessories that can be attached, individually or in various combinations, to said transducer-carrying head.

23 Claims, 5 Drawing Sheets

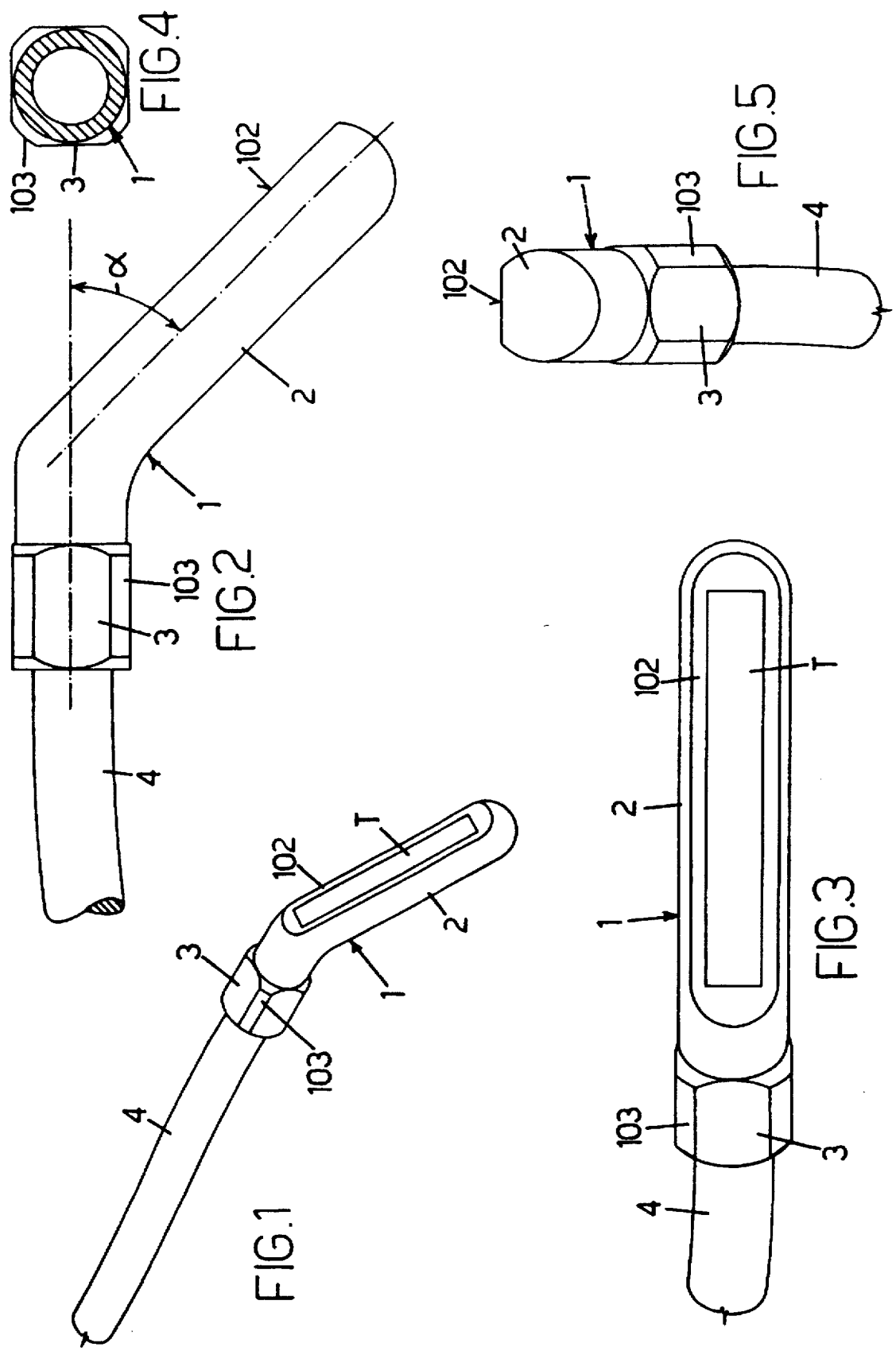

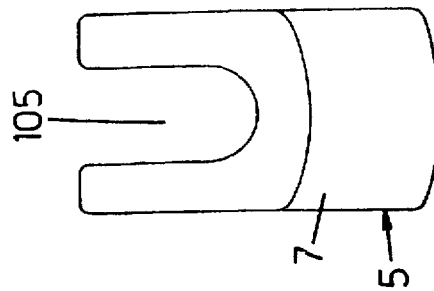
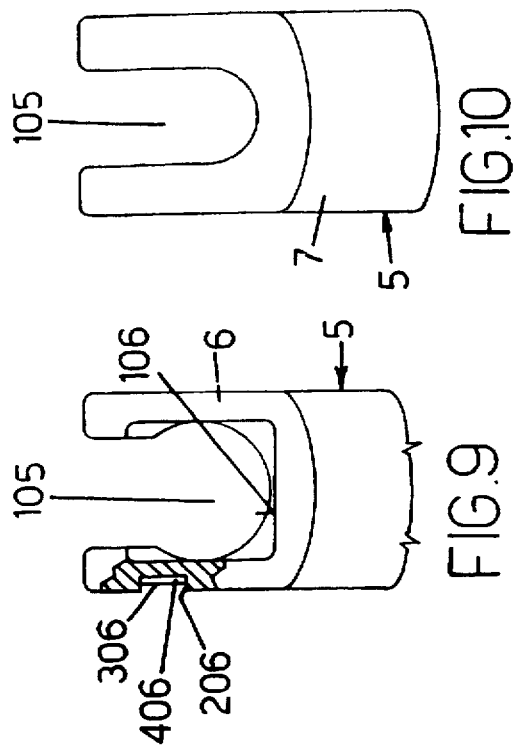
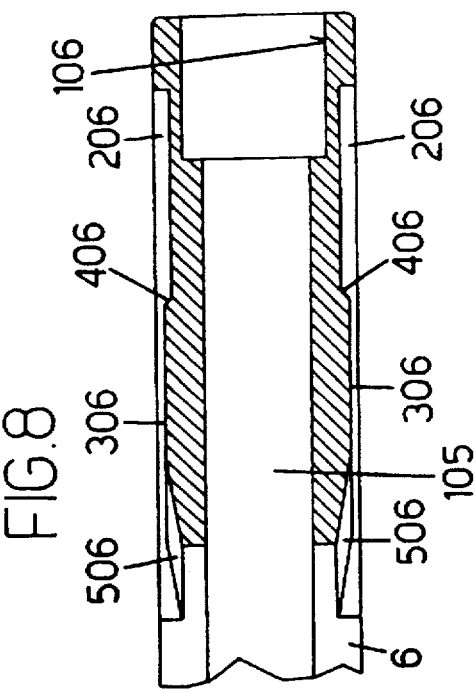
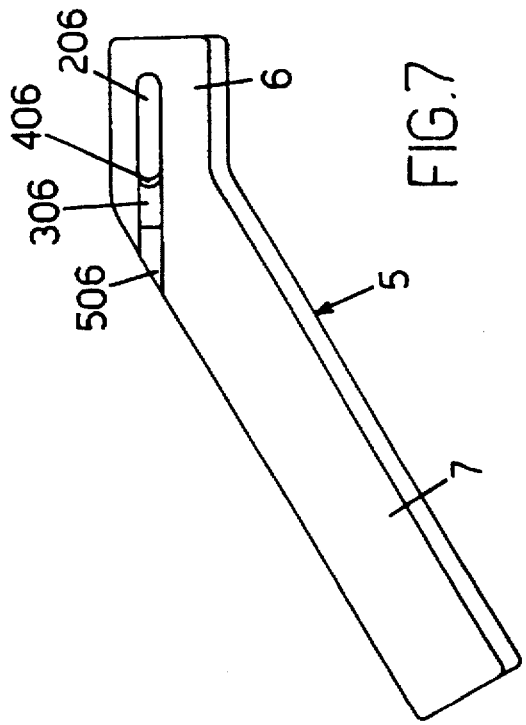
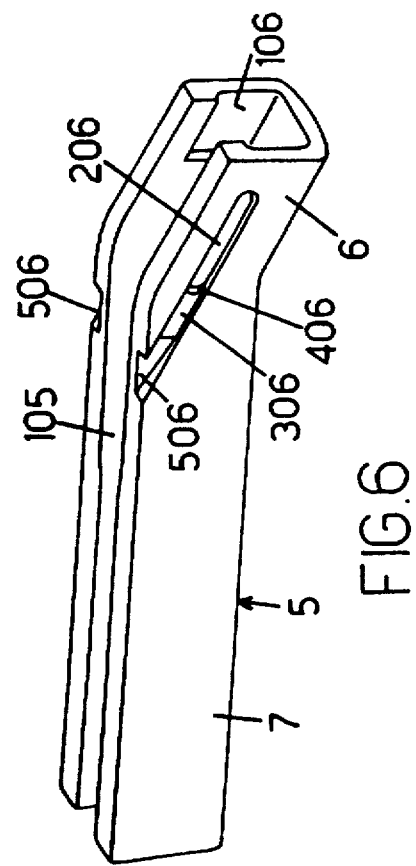

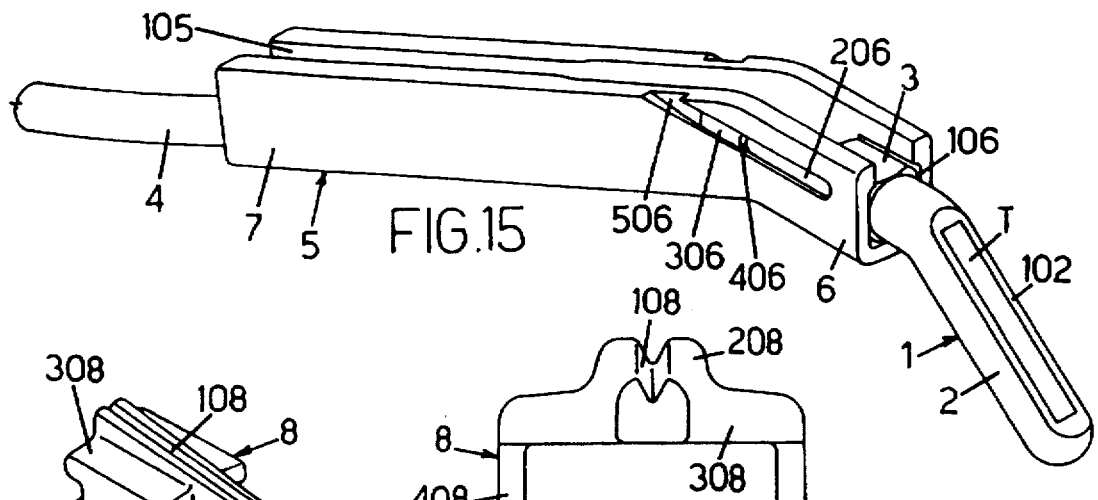
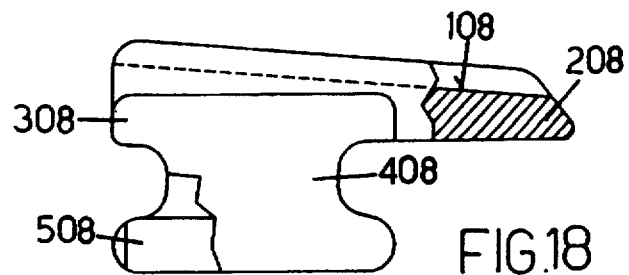
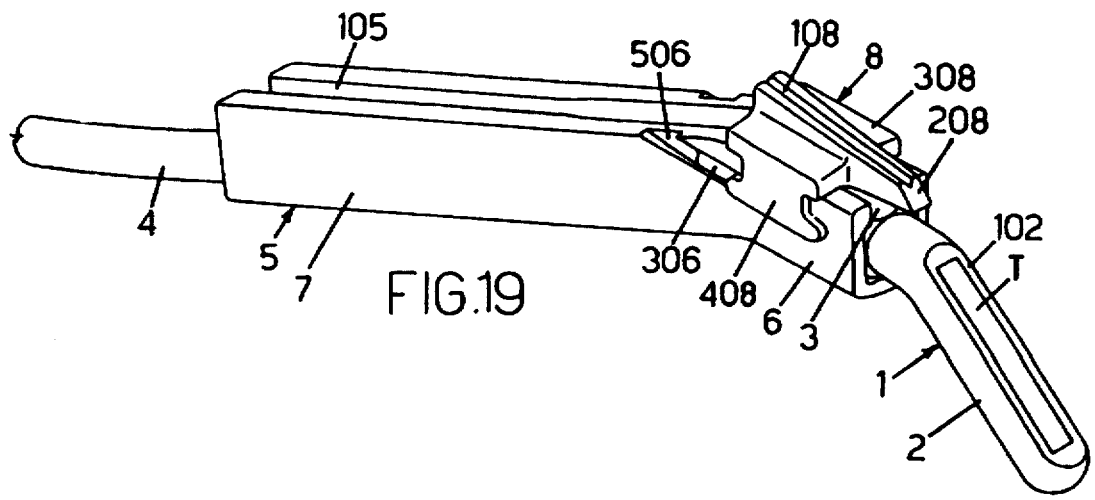

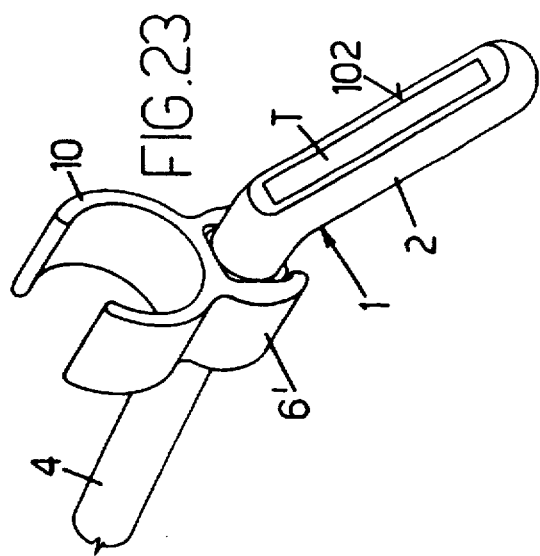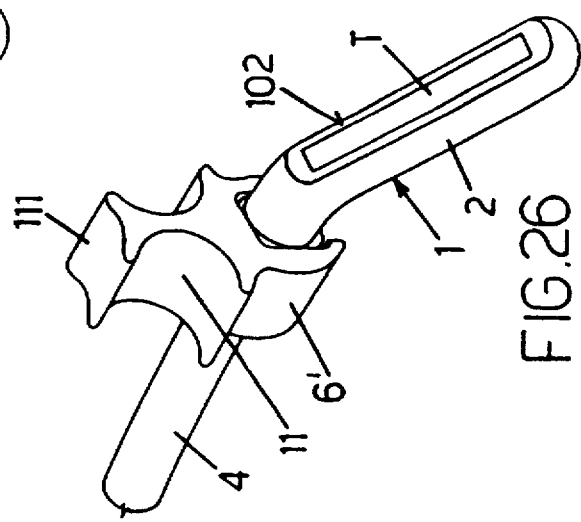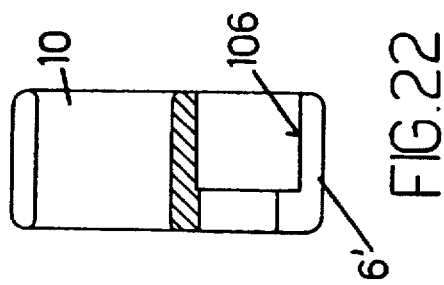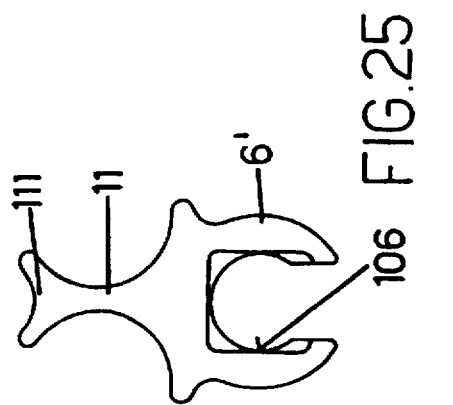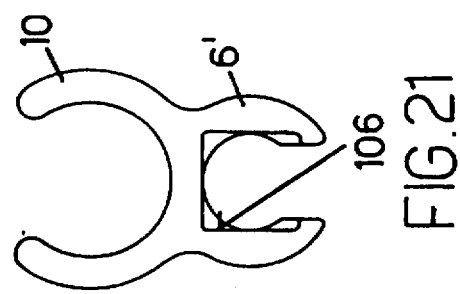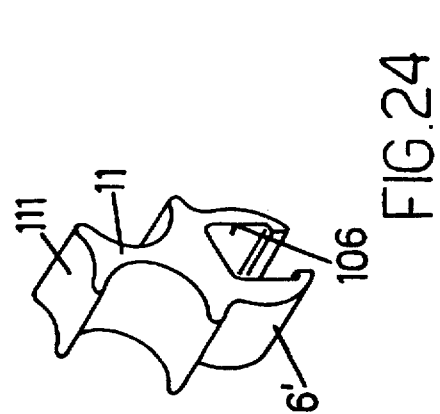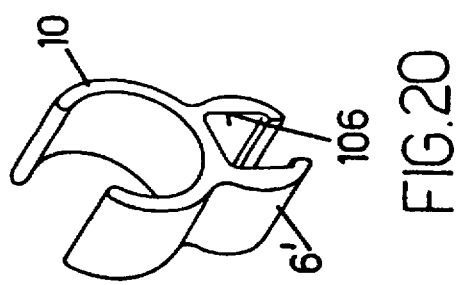

INTRAOPERATIVE PROBE, SPECIFICALLY INTENDED FOR DIRECT-CONTACT OBSERVATIONS

BACKGROUND OF THE INVENTION

The subject-matter of the present invention is an intraoperative probe, specifically intended for direct-contact observations, including a head for housing the transducers and a portion of a handle or grip, as well as a cable for connecting the transducers to processing and/or displaying devices.

Probes of this type are particularly suitable to allowing observation of soft tissue sections by direct contact with the organ involved during a surgical operation.

These probes not only make it possible to accurately determine the position of the lesions in the organs involved as well as of the blood vessels, thus increasing the safety and reliability of the operations, they can also be used in vascular surgical procedures, helping surgeons to quickly recognized and identify major anatomical defects and technical imperfections requiring immediate action before completing the surgical procedure.

In state-of-the-art intraoperative probes of this type the transducer-carrying head and the portion of handle or grip form one integral part and have a predetermined shape; as a result, the probe's head always has the same orientation relative to the grip. Because of the consequent limitations on the use of the probe in various operating conditions, different types of probes are provided, with different predetermined shapes and head orientations of the head relative to the grip.

Therefore, the purpose of the present invention is to produce an intraoperative zone [sic] of the type described above, in such a way as to make said probe easily adaptable, by extremely economical means, to different operating conditions, making it possible to use additional instruments that expand the range of applications of the probe itself.

SUMMARY OF THE INVENTION

The present invention achieves the above purposes by means of an intraoperative probe of the type described at the outset, where the portion of the handle is separate from the transducer-carrying head, said two parts being equipped with matching means of removable attachment.

Any means of removable attachment can be used, particularly the connector type, since one of said two parts has a connecting end, preferably not round in shape, while the other part has a matching connecting seat, which is annular in shape or is configured as an open ring, that is, one that is not round, at least not on the inside.

The portion of the handle or grip may be equipped with a means for housing the cable connected to processing and/or displaying devices.

As an additional characteristic feature, the transducer-carrying head of the probe has a basically cylindrical, elongated shape, the transducers being placed along an axial portion of the shell wall of said transducer-carrying head. This portion may be flat or have a predetermined curvature generated around an axis which is perpendicular to the axis of the probe's head, the shape of the connecting end being other than a round shape, such as a polygonal or similar shape, and its axis being oriented with a preset angle relative to the axis of the probe's cylindrical head.

The axis of the head portion and the axis of the connecting end form a 45° angle.

In particular, the axis of the transducer-carrying head and the axis of the connecting end lie on the same plane, which is parallel to the transducers' sensing direction, that is, to the plane which is perpendicular to the flat portion on which the transducers are arrayed, while at least one of the faces of the connecting end is parallel to said plane.

To further improve the variety of shapes that can be obtained by virtue of the different orientations of the probe relative to the handle, the connecting seat on the end of the handle, that is, the axis of said seat, is angled at approximately 30° relative to the remaining part of he handle itself, that is, to the axis of said remaining part.

The above arrangements make it possible to produce an intraoperative probe with a configuration that can be modified within a predetermined number of shapes.

In particular, when the connecting seat and the matching connecting end have a basically square shape, the probe can present four different configurations, corresponding to standard configurations commonly used for this type of probe. Consequently, it is possible to obtain a multiplicity of different configurations with one probe alone. The number of such configurations obviously can be increased by providing a connecting seat and connecting end with a higher number of facets.

The connecting cable runs from the connecting end of the transducer-carrying head, and the connecting seat, as well as the corresponding portion of handle or grip, have an open cross section which is basically U-shaped. The opening through which the cable is introduced should be on the outside of the handle with the connecting seat, with reference to the angle formed by said two parts, while the width of the cable-holding groove in the handle is designed to hold the cable there by virtue of a slight retentive action resulting from a compression and/or slight elastic deformation of the same. The cross section of the cable-holding groove preferably should be slightly C-shaped or in the shape of a sector of a circle with an angle greater than 180°, so as to allow insertion and removal of the cable by virtue of the elastic deformation of the same as well as of the handle.

However, the probe's handle may also consist of anatomically contoured elements that can be gripped by or attached to at least one finger of the hand. In a first embodiment of the invention, the connecting seat of the probe is laterally attached to an annular element that can be expanded, at least elastically; such element having an open-ring section with an angle greater than 180° and being the element for elastic engagement with one finger of the hand.

Opposite the connecting seat, the gripping element has a transversal widening designed to accommodate two fingers, on the side of the back and/or the palm of the hand. In particular, said gripping element has a basically T-shaped section, where the two lateral grooves are rounded, or a section shaped as a double C, where the two Cs are side by side facing opposite directions, that is, with their open sides pointing away from each other.

By virtue of the angle between th e axis of the connecting end and the probe's transducer-carrying head, this type of finger-fitting grip also allows for different configurations of the handle-probe assembly, in a fashion similar to what has been described above with reference to the handle.

The handle and/or the additional different grips that can be associated with the probe's transducer-carrying head are also equipped with means of removable attachment to surgical instruments or additional accessories.

In particular, said means of attachment may be a connector, lock-joint or matching shape type of coupling.

In a preferred embodiment, needle-guiding elements for a biopsy needle can be attached to the handle, in particular to the outside of the connecting seat on the probe's head.

Said elements can be attached to the handle in a removable fashion by means of a slide, and have a needle-supporting guide on the external periphery as well as on the side of the connecting seat opposite the handle itself. Said guide consists of a groove that basically runs parallel to the axis of the connecting seat for the transducer-carrying head. The axis of the needle-guiding groove can advantageously lie on the same plane containing the axis of the handle and the connecting seat, and can also present on said plane a preset angle relative to the axis of said connecting seat for the transducer-carrying head.

The advantages of the present invention are apparent in the above description. This particular probe configuration makes it possible to provide for a set of holding and gripping accessories, as well as couplings for additional elements that can be attached as modules to a transducer-carrying head, so as to obtain an extremely economical and versatile probe whose functions or range of applications can easily be integrated over time and according to the particular needs.

The probe according to the present invention has additional characteristics, as claimed below.

BRIEF DESCRIPTION OF THE DRAWINGS

The characteristics of the invention and the corresponding advantages can be seen more clearly in the following description of some embodiments, presented as nonrestrictive examples and illustrated in the attached drawings, where:

FIGS. 1 to 5 show different views of the probe's head according to the invention.

FIGS. 6 to 10 show different views of the probe's handle according to the invention.

FIG. 15 shows a probe configuration particularly suited to attachment of an accessory such as a needle guide for biopsy needles.

FIGS. 16 to 18 show different views of the removable needle guide that can be attached to the probe's handle.

FIG. 19 illustrates a probe, in accordance with FIG. 15, with the needle guide of the preceding figures mounted thereon.

FIGS. 20 to 23 show a second embodiment of the probe's gripping elements, in the form of means of removable attachment to one finger of the hand.

FIGS. 24 to 26 show a variation of said elements for the probe's head, designed for gripping by means of the fingers of the hand according to the invention.

DESCRIPTION OF THE PREFERRED EMBODIMENT

Figure 14:
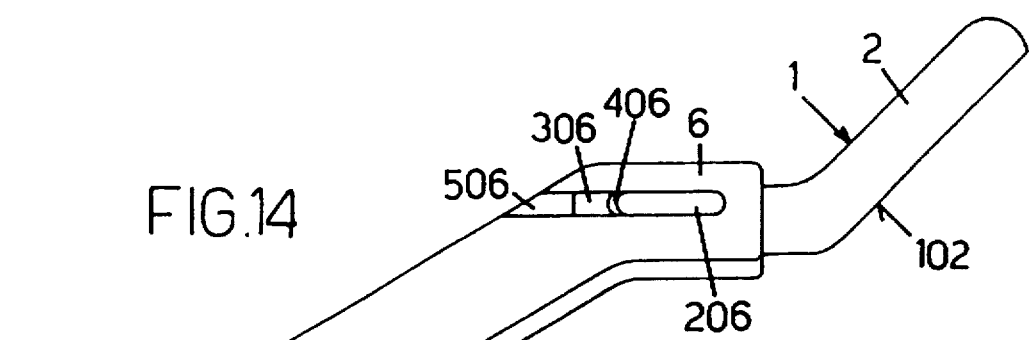
FIGS. 11 to 14 show a side view of different configurations for coupling the probe's head with the handle, designed in accordance to the preceding figures, said configurations corresponding to standard configurations of intraoperative probes.
Figure 13:
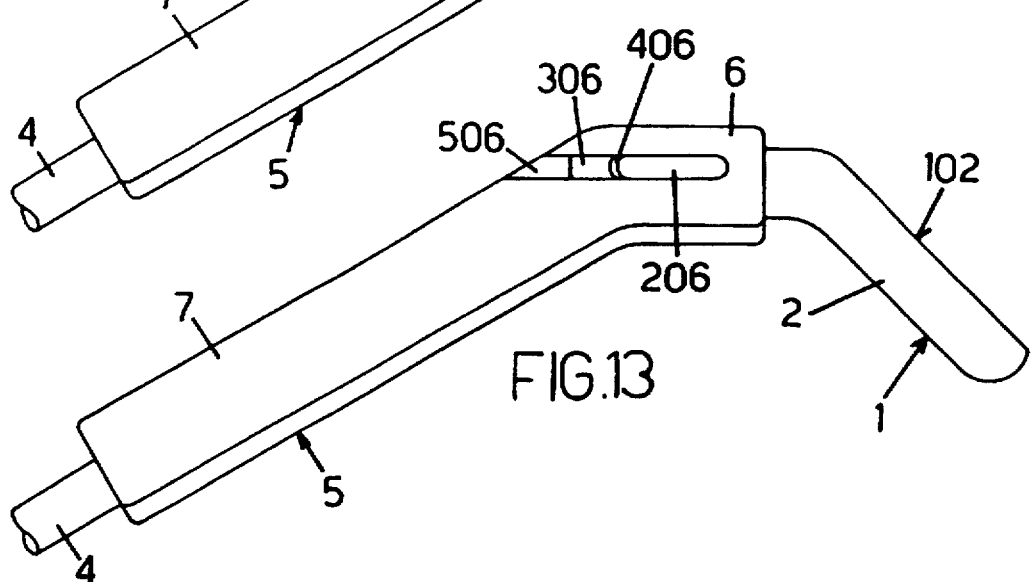

With reference to FIG. 1 to 5, an intraoperative probe's transducer-carrying head (1) includes an elongated body, basically cylindrical in shape (2), housing the transducers (T), which are arranged in a row along the axis of said elongated body (2). The active surface of the transducers (T) is to be placed on a flattened area (102) extending in the direction of the axis of the housing body (2), while at the end opposite the insertion end, the basically cylindrical body (2) terminates in a connecting nonannular element (3). The cable (4) connecting the transducers (T) to processing and/or displaying devices exits in a basically coaxial direction the head side of the connecting end (3), said housing head (2) and connecting end (3) being at an angle relative to each other, while their axes lie in a plane that is basically perpendicular to the flattened area (102), so as to form an angle ($\alpha$) of 45° between said axes, that is, between the plane parallel to said flattened area (102) of the transducer-carrying head (2) and the axis of the connecting end (3).

The shape of the flattened area (102), shown as perfectly flat in the illustration, can obviously be, as it is known to be, a curved shape generated around an axis perpendicular to the axis of the transducer-carrying head (2) and having a considerably larger radius.

The connecting end (3) is not round in shape; in particular, it has a square shape, the corner areas (103) between the faces being flattened or rounded.

With reference to FIGS. 6 to 10, the handle (5) consists of an elongated element (7) having a transversal U section or preferably a C-shaped section, that is, one that narrows on the open side or presents an angle greater than 180°, and also has a connecting seat (106) matching the connecting end (3) of the transducer-carrying head (1). Said connecting seat (106) has a basically square section and is obtained in a terminal portion (6) of the handle (5), said portion being at an angle relative to the axis of the handle (5) itself. The axis of the connecting seat (106) and the axis of said portion (7) of the handle (5) lie in the same plane and are at an angle relative to each other, so that the prolongation of the axis of portion (6) of the handle forms an angle ($\beta$) of approximately 30° with the axis of the connecting seat (106).

The handle (5) has a cable-holding groove (105) extending continuously from one end to the other of the handle itself and communicating with the connecting seat (106). The groove (105) and the connecting seat (106) itself are open along their whole length, with no break in continuity on the outside of the handle (5) with reference to the angle between the connecting terminal portion (6) and portion (7) of the handle, said opening making it possible to quickly and easily engage the connecting cable inside the handle (5) itself.

The groove (105) offers the advantage of having a cross section that basically matches the section of the cable, and by virtue of its C shape, with an angle greater than 180°, the opening for insertion of cable (4) is slightly narrower relative to the diameter of the cable (4) itself, so as to enable the insertion and removal of the cable by virtue of a slight elastic deformation of the same and/or the handle, but also effectively retaining it inside the groove (105).

Figure 12:
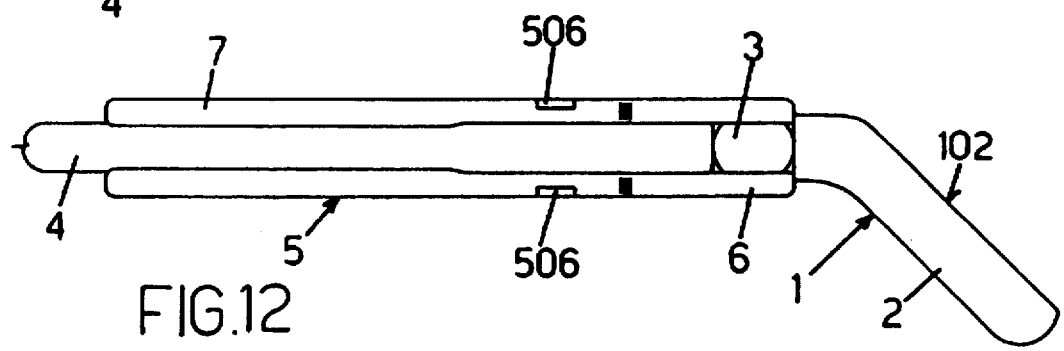
Figure 11:
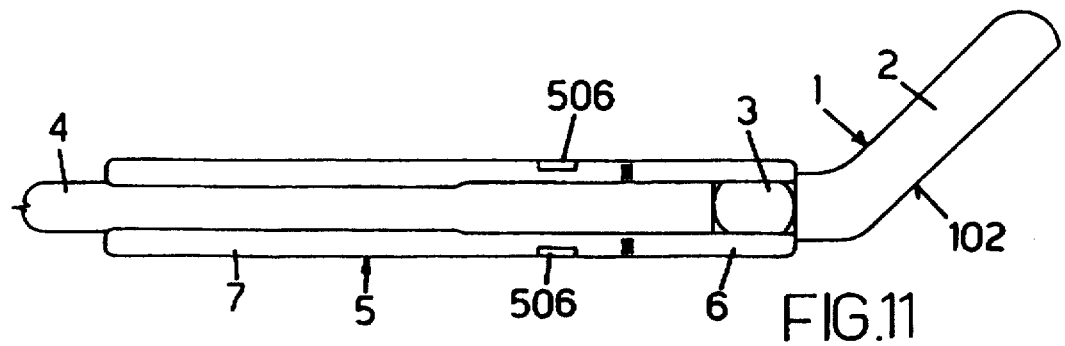

FIGS. 11 to 14 illustrate four different examples of configurations of the probe of the present invention. These configurations can be obtained by simply changing the angle between the handle (5) and the transducer-carrying head (1). FIGS. 11 and 12 illustrate two configurations that are intermediate configurations between the L configuration shown in FIG. 13 and the J configuration shown in FIG. 14. These configurations basically correspond to the standard configurations of intraoperative probes currently available on the market. Obviously, with a connecting end (3) having a polygonal shape —for instance, hexagonal, octagonal or similar shape —and a connecting seat (106) with a matching section it is possible to obtain a larger number of intermediate probe configurations, differing from one another in respect of the different angle between the transducer-carrying head (2) and the handle (5).

The non-annular shape of the elements (3, 106) connecting the transducer-carrying head (2) to the handle (5) makes it possible to change the probe configuration quickly and conveniently, while assuring a remarkable stability of the connecting position of the transducer-carrying head (2) relative to the handle (5).

The probe of the present invention can be associated with additional removable and replaceable accessories, such as a needle guide (8) for a biopsy needle. In this particular case, as shown in FIGS. 15 to 19, the needle guide (8) can be directly and removably mounted, in a snap-on fashion, on the terminal portion (6) of the handle (5) forming the connecting seat (106) for the transducer-carrying head (2).

As shown in FIG. 15, the optimal probe configuration is the L configuration. The needle guide (8) consists of a guiding groove preferably U or V shaped and oriented in the direction of the axis of the terminal portion (6) where the connecting seat for the probe's head (2) is to be located. The guiding groove (108) is machined into a rib (208) projecting from a slide (308). Said slide (308) is equipped with snap-on elements for attaching to the outside of the connecting portion (6) of the handle (5) relative to the angle between said portion and part (7) of the handle, and is positioned over the opening of the groove (105) holding the cable (4).

The slide (308) has two lateral tabs (408), that is to say, it is basically shaped as an upside-down U. The free ends of said lateral tabs (408) have teeth (508) projecting toward the sides of the handle (5) that laterally delimit said cable-holding groove (105) and connecting seat (106), these being the sides where the mounting slots (206) are to be located. The mounting slots (206) for the slide (308) are parallel to the axis of the connecting portion and terminate as open slots on the outside of the same, that is, basically in the radius area between the grip (6) and the handle (5). Said slots are closed on the side of the transducer-carrying head (1) and determine the working position of the needle guide (8). With particular reference to FIG. 8, the invention provides for means of removable locking of the needle guide (8), hence of the slide (308), in its working position. In particular, in the middle portion of said slots there is to be a projection (306) forming a retaining tooth (406) designed to prevent detachment of the slide (308), the distance between said tooth and the closed head side of the corresponding slot (206) being basically equal to the length of the lugs (508) on said slide (308) designed to engage the grooves (106). On the open side, the end of said projection (306) has a lead-in surface, in the shape of an inclined plane (506), contributing to the progressive elastic spreading of the slide's tabs (408) that allows them to pass beyond said lug (306). The retaining tooth (406) is also slightly angled, but to a lesser degree than said lead-in surface, so as to allow detachment of the needle guide (8) only when a greater force is applied, thus preventing instances of accidental or undesired detachment.

According to an additional characteristic, slots (206) lie on a plane that is basically parallel to the opening of the cable-holding groove (105). This makes it possible to place the needle guide (108) in a position that is basically aligned with the middle plane perpendicular to the flattened area (102) of the body (2) housing the transducers (T). Preferably, on said plane the needle-guiding groove (308) [sic] has a preset angle relative to the axis of the connecting seat (106) for the transducer-carrying head (1), so that it converges toward said axis in the direction of the head carrying the transducers (T), thus forming an angle of less than 45° with said flattened area.

This arrangement makes it possible to use the probe of the invention as a guiding and supporting structure for the needle, thus making it considerably easier to obtain tissue samples.

FIGS. 20 to 23 illustrate a second embodiment of the probe according to the invention. Here, the handle (5) is replaced by means of attachment to one finger of the hand. The probe's connecting seat (106) is designed in a manner similar to that previously described; however, instead of being located in a terminal portion of the handle (5), said connecting seat is designed in the shape of an open ring or bushing (6'). Said ring (6') is attached to an open thimble or ring (10) having a diameter basically corresponding to the diameter of the hand's fingers. Preferably, the open ring can be slightly spread by elastic deformation, so as to make possible its elastic coupling with the finger as well as its adaptation to the size of the same. In the embodiment illustrated in said figures, the open ring (6') with the connecting seat (106) for the transducer-carrying head and the open ring (10) for attachment to one finger are arranged with their axes basically parallel to each other and the respective openings diametrically opposite each other. Of course, this is not to be regarded as a restrictive arrangement, in that it is possible to provide for different reciprocal orientations and positions of the two rings (6', 10).

In the variation shown in FIGS. 24 to 26, in place of said open ring or thimble (10), the open ring (6') with the connecting seat for the transducer-carrying head (1) has a radial projection (11) in the shape of two opposing Cs forming two side-by-side, axially parallel grooves, as well as a widened area (111) on its free end. Said projection (11) is designed to make it possible to grasp the probe with two fingers of the hand, tightened around the radial projection (11) itself.

To allow a better grip of the probe the opposing grooves extend further toward the outside of the radius area between the open ring (6') and the connecting seat.

The two embodiments shown in FIGS. 20 to 26 can be attached to both the back and the palm of the hand.

Although they are not illustrated in detail, these two embodiments obviously may provide for removable means of attachment for accessories such as a needle guide (8) for biopsy needles, or the like. The probe may be constructed in a manner basically as described in the example shown in FIGS. 1 to 19, with the simple addition of specific dimensional and shape adaptations.

The invention obviously is not limited to the above descriptions and illustrations, but may be modified, especially in its construction, without thereby departing from its core principle as described above and claimed below.

We claim:

1. An intraoperative probe for use with direct-contact observations, said probe comprising:

a head for housing transducers;

a handle;

a cable connected to said head;

said handle and said head being removably attachable; and said head and said handle being selectively rotatable relative to one another into a plurality of discrete configurations.

2. The probe of claim 1, wherein said removably attachable handle and head comprise:

connector elements, one of said handle and said head having a connecting end of polygonal shape, and the other of said handle and said head having a connecting seat, said connecting seat having an inside surface matching said polygonal shape, said connecting end insertable into said connecting seat, said polygonal shaped connecting end having a number of major sides, whereby said number of major sides equals a total number of said discrete configurations.

3. The probe of claim 2, wherein an axis of said connecting end is slanted relative to a sensing direction of said transducers, said axis and a plane parallel to said sensing direction forming an angle ($\alpha$) of approximately 45°.

4. The probe of claim 3, wherein said handle includes a needle guide for attachment of a biopsy needle.

5. The probe of claim 4, wherein said needle guide includes a channel having a V-shaped cross section, in which channel a biopsy needle is adapted to slide longitudinally, said needle guide being attachable to said handle proximate said connecting seat, said channel extending in a direction which traverses said sensing direction.

6. The probe of claim 5, wherein said channel points toward said transducers.

7. The probe of claim 5, wherein said needle guide includes a slide that is attachable to said handle proximate said connecting seat, said slide straddling two sides of said handle.

8. The probe of claim 2, wherein said head has a substantially cylindrical, elongated shape, an axis of said connecting end forming a 45° angle with a longitudinal axis of said cylindrically shaped head.

9. The probe of claim 8, wherein said transducers are arranged along an axial portion of said cylindrical head, said axial portion forming an area ranging from substantially flat to having predetermined curvature about an axis perpendicular to said longitudinal axis of said head, said connecting end forming approximately a 45° angle ($\alpha$) with a plane tangent to said substantially flat area.

10. The probe of claim 2, wherein said polygonal shape is substantially square with chamfered corners, whereby said total number of discrete configurations equals four.

11. The probe of claim 2, wherein said head has a substantially cylindrical elongated shape and said handle and said head lie substantially in a common plane.

12. The probe of claim 2, wherein said connecting seat is formed on an end of said handle, said connecting seat forming an angle ($\beta$) of approximately 30° with an axis of a remaining portion of said handle.

13. The probe of claim 2, wherein said handle is attachable to at least one finger of a hand.

14. The probe of claim 13, wherein said head includes said connecting end and said handle includes said connecting seat, said handle comprising an elastically spreadable annular element, said element being in the shape of an open ring, said ring circumscribing an angle greater than 180°, whereby said ring allows elastic attachment to a finger of a hand.

15. The probe of claim 14, wherein both said connecting seat and said element are open rings tangentially attached to one another, said rings having their open portions positioned diametrically opposite.

16. The probe of claim 2, wherein said handle comprises a lateral gripping projection, said projection comprising two oppositely faced substantially radial sides and a transversely broadened area located at a terminal end of said projection, whereby said radial sides are anatomically contoured to two fingers of a hand extended side-by-side and said broadened area is positioned over the fingers.

17. The probe of claim 1, wherein said handle includes a groove, said groove houses said cable therein for connection to processing and/or displaying devices and said cable is connected to said head.

18. The probe of claim 17, wherein said groove comprises an open U-shaped cross-section extending entirely across an axial length of said handle.

19. The probe of claim 18, wherein said connector is one of a bayonet-joint, lock-joint, snap-on, push-on, and matching-shape connector.

20. The probe of claim 18, wherein said cross section is a section of a circle having an angle greater than 180°, whereby said cable is insertable and removable in said handle.

21. The probe of claim 17, wherein said handle is comprised of a connecting seat and an elongated portion, said groove being located on an outside of said handle, including said connecting seat and said elongated portion.

22. The probe of claim 17, wherein said groove has a width such that said cable is retained in said groove.

23. The probe of claim 1, wherein said handle includes a connector for removable attachment of surgical instruments.

* * * * *